US00PP08619P

United States Patent [19]

Meilland

[11] Patent Number: Plant 8,619

[45] Date of Patent: Mar. 1, 1994

[54] HYBRID TEA ROSE PLANT NAMED 'MEIVAMO'

[75] Inventor: Alain A. Meilland, Antibes, France

[73] Assignee: The Conard-Pyle Company, West Grove, Pa.

[21] Appl. No.: 981,059

[22] Filed: Nov. 24, 1992

[51] Int. Cl.[5] ..... A01H 5/00

[52] U.S. Cl. ..... Plt./18

[58] Field of Search ..... Plt. 18, 17, 11

*Primary Examiner*—Howard J. Locker

*Attorney, Agent, or Firm*—Burns, Doane, Swecker & Mathis

[57] ABSTRACT

A new and distinct variety of Hybrid Tea rose plant is provided which abundantly forms elegant long lasting double blossoms which are Poppy Red widely suffused with light Carmine Rose. The new variety originated as a spontaneous mutation of the Keiromo variety (U.S. Plant Pat. No. 7,138). The buds are large and of good form. The plant exhibits strong and vigorous vegetation and is well suited for cut flower production. The ability to undergo forcing is excellent particularly during the winter. The plant forms dense and glossy foliage and is not partiuclarly affected by cryptogamic diseases.

1 Drawing Sheet

SUMMARY OF THE INVENTION

The new variety of the Hybrid Tea rose plant was discovered in France as a spontaneous mutation of unknown causation of the Keiromo variety (U.S. Plant Pat. No. 7,138). I was attracted to the new variety by its distinctive blossom coloration. Had this new variety not been located and preserved by me, it would have been lost to mankind.

As discussed in U.S. Plant Pat. No. 7,138, the parent Keiromo variety was created during the course of a controlled plant breeding program. The female parent (i.e., the seed parent) of the Keiromo variety was the Jofitali variety (U.S. Plant Pat. No. 4,083). The male parent (i.e., the pollen parent) of the Keiromo variety was the Happiness variety (U.S. Plant Pat. No. 911). The parentage of the parent Keiromo variety can be summarized as follows:

Jofitali × Happiness.

It was found that the new variety of the present invention exhibits attractive blossoms which are Poppy Red widely suffused with light Carmine Rose when fully open. In contrast, the fully open blossoms of the parent Keiromo variety are Scarlet Pink on the upper surface and light Carmine Rose on the under surface. Also, the blossom petals on mature blooms of the new variety tend to enclose the central portion of the blossoms (i.e., the pistils and stamens) as illustrated in FIG. 9 unlike those of the parent Keiromo variety. Other than as indicated with respect to the blossom coloration and petal disposition, the growth habit and the bloom production of the new variety are substantially identical to those of the Keiromo variety.

It was found that the new variety of Hybrid Tea rose plant of the present invention possesses the following combination of characteristics:

(a) forms in abundance elegant long lasting double blossoms which are Poppy Red widely suffused with light Carmine Rose, (b) forms blossom petals on mature blooms that tend to enclose the central portion of the blossom unlike those of the Keiromo variety, (c) exhibits a growth habit substantially identical to that of the Keiromo variety (U.S. Plant Pat. No. 7,138), (d) is well adapted for greenhouse forcing to produce cut flowers, (e) exhibits strong and vigorous glossy vegetation, and (f) is not particularly affected by cryptogamic diseases.

The new variety well meets the needs of the cut flower industry since the blossoms are highly attractive and are formed in abundance on a substantially continuous basis.

The new variety has been found to undergo asexual propagation in France and in the United States by a number of routes, including budding, grafting, cuttage, etc. The characteristics of the new variety have been found to be strictly transmissible by such asexual propagation from one generation to another.

The new variety has been named the Meivamo variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during April while grafted on *Rosa indicia* understock and growing in greenhouses at Cap d'Antibes, France.

FIG. 1 — illustrates a specimen of a young shoot;

FIG. 2 — illustrates a specimen of a floral bud before the opening of the sepals;

FIG. 3 — illustrates a specimen of a floral bud at the opening of the sepals;

FIG. 4 — illustrates a specimen of a floral bud at the opening of the petals;

FIG. 5 — illustrates a specimen of a flower in the course of opening;

FIG. 6 — illustrates a specimen of a fully open flower — plan view — reverse;

FIG. 7 — illustrates a specimen of a fully open flower — plan view — obverse;

FIG. 8 — illustrates a specimen of a fully open flower immediately prior to petal drop — plan view — reverse;

FIG. 9 — illustrates a specimen of a fully open flower immediately prior to petal drop — plan view — obverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch (adult wood);

FIG. 14 — illustrates a specimen of a leaf with three leaflets — plan view — upper surface;

FIG. 15 — illustrates a specimen of a leaf with five leaflets — plan view — under surface; and FIG. 16 — illustrates a specimen of a leaf with seven leaflets — plan view — upper surface.

DETAILED DESCRIPTION

Figures 1, 2, 3, 4, 5, 6, 7, 8, 9, 10, 11, 12, 14, 15, 16:
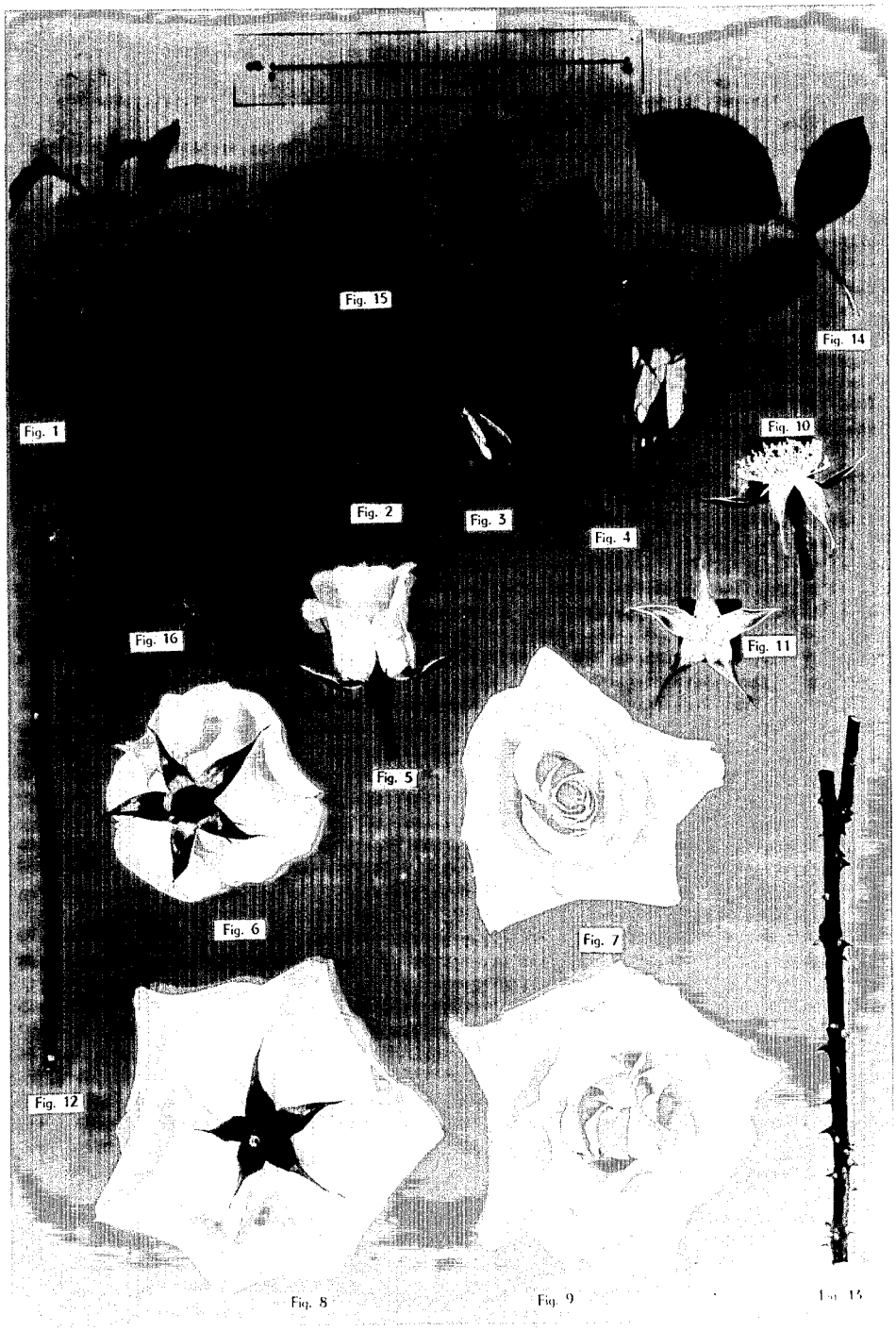

The chart used in the identification of the colors is that of The Royal Horticultural Society (R.H.S. Colour Chart). The description is based on two year old plants made during April while grafted on *Rosa indicia* understock and growing in greenhouses at Cap d'Antibes, France. The coloration in common terms precedes reference to the chart.

Class: Hybrid Tea.

Plant:

*Height.*—Plants which were pruned to a height of 85 cm. produce floral stems having a length of approximately 50 to 70 cm, and when grown in the field at the end of the growing season at Wasco, Calif., the plant height commonly is approximately 130 cm.

*Habit.*—Upright.

Branches:

*Color.*—Young stems: light green, Green Group 143A, more or less shaded with reddish coloration. Adult wood: medium green, Green Group 137B.

*Thorns.*—Size: average. Quantity: moderately numerous. Color: greenish in coloration on young stems and tan on mature wood.

Leaves:

*Stipules.*—Adnate, pectinate, fairly wide and linear.

*Petioles.*—Upper surface: striped, reddish brown on young leaves and medium green with glandular edges on adult foliage. Under surface: light green, bear a few thorns.

*Leaflets.*—Number: 3, 5, and 7 (most often). Shape: oval. Serration: single and regular. Texture: consistent. General appearance: dense bright foliage. Color (young foliage): upper surface: medium green, Green Group 137A. under surface: light green, Green Group 137C. and widely tinted with reddish brown. Color (adult foliage): upper surface: dark green, Green Group 139A. under surface: light green, Green Group 137C.

Inflorescence:

*Number of flowers.*—Generally one per stem.

*Peduncle.*—Straight, rigid, light green in coloration, and bears numerous glandular acicules. The length is approximately 11 to 12 cm. on average.

*Sepals.*—Upper surface: tomentose, greenish in coloration. Under surface: light green in coloration, the edges of the outer sepals are glandular and slightly appendiculated.

*Buds.*—Shape: conical. Length: approximately 4.5 cm. on average. Size: large. Color upon opening: upper surface: Scarlet Pink, Red Group 43C. under surface: Scarlet Pink, Red Group 43B.

*Flower.*—Shape: initially elongated, changing to cuplike with an apple-shaped center, and fully double. Diameter: approximately 12 to 13 cm. on average. Color (when opening begins): upper surface: Poppy Red, Red Group 38C, and widely suffused with Coral Pink, Red Group 38D. Under surface: Poppy Red, Red Group 38C, and widely suffused with Coral Pink, Red Group 38D, and lighter towards the base of the petals. Color (when blooming): upper surface: Poppy Red, Red Group 38C, and widely suffused with Coral Pink, Red Group 38D. under surface: Poppy Red, Red Group 38C, and widely suffused with Coral Pink, Red Group 38D, and lighter towards the base of the petals. Color (at end of opening): upper surface: Poppy Red, Red Group 38C, and widely suffused with light Carmine Rose, Red Group 52D. under surface: Poppy Red, Red Group 38C, and widely suffused with light Carmine Rose, Red Group 52D, and lighter towards the base of the petals. Fragrance: very slight. Lasting quality: long on the plant and when cut and placed in a vase. Petal number: approximately 32 to 35 on average. Texture: consistent. Petal drop: fairly good. Stamen number: approximately 234 on average. Anthers: normal, yellowish in coloration and bear pollen. Filaments: free-standing, bright yellow with fuschia tips, of irregular heights. Pistils: approximately 172 on average. Stigmas: normal, straw colored, located below the stamens. Styles: free-standing, light fuschia in coloration, of irregular heights. Receptacle: light green, fairly smooth, and in longitudinal section is pitcher-shaped.

Development:

*Vegetation.*—Strong and vigorous.

*Blooming.*—Substantially continuous when forced in a greenhouse for fresh-cut flower production.

*Aptitude to forcing.*—Excellent, especially during the winter.

*Resistance to diseases.*—Good.

I claim:

1. A new and distinct variety of Hybrid Tea rose plant characterized by the following combination of characteristics:

(a) forms in abundance elegant long lasting double blossoms which are Poppy Red widely suffused with light Carmine Rose, (b) forms blossom petals on mature blooms that tend to enclose the central portion of the blossoms unlike those of the Keiromo variety, (c) exhibits a growth habit substantially identical to that of the Keiromo variety (U.S. Plant Pat. No. 7,138), (d) is well adapted for greenhouse forcing to produce cut flowers, (e) exhibits strong and vigorous glossy vegetation, and (f) is not particularly affected by cryptogamic diseases; substantially as herein shown and described.

* * * * *